(12) United States Patent
Chikugo et al.

(10) Patent No.: US 10,996,164 B2
(45) Date of Patent: May 4, 2021

(54) OIL STATE DETECTION DEVICE, WORK MACHINE, MANAGEMENT SYSTEM, AND OIL STATE DETECTION METHOD

(71) Applicant: Komatsu Ltd., Tokyo (JP)

(72) Inventors: Hiroyuki Chikugo, Tokyo (JP); Shuuji Hori, Tokyo (JP); Haruna Higashi, Tokyo (JP)

(73) Assignee: Komatsu Ltd., Tokyo (JP)

( * ) Notice: Subject to any disclaimer, the term of this patent is extended or adjusted under 35 U.S.C. 154(b) by 74 days.

(21) Appl. No.: 16/483,184

(22) PCT Filed: Feb. 20, 2018

(86) PCT No.: PCT/JP2018/005911
§ 371 (c)(1),
(2) Date: Aug. 2, 2019

(87) PCT Pub. No.: WO2018/198498
PCT Pub. Date: Nov. 1, 2018

(65) Prior Publication Data
US 2020/0232911 A1    Jul. 23, 2020

(30) Foreign Application Priority Data
Apr. 28, 2017   (JP) .............................. JP2017-090330

(51) Int. Cl.
| | |
|---|---|
| *G01N 21/27* | (2006.01) |
| *F01M 11/10* | (2006.01) |
| *F15B 21/04* | (2019.01) |
| *G01N 33/28* | (2006.01) |

(52) U.S. Cl.
CPC ............. *G01N 21/27* (2013.01); *F01M 11/10* (2013.01); *F15B 21/04* (2013.01); *G01N 33/2888* (2013.01); *F01M 2250/00* (2013.01); *G01N 2201/062* (2013.01)

(58) Field of Classification Search
CPC ............... G01N 21/27; G01N 33/2888; G01N 2201/062; F01M 11/10; F01M 2250/00
USPC ........................................................... 356/70
See application file for complete search history.

(56) References Cited

U.S. PATENT DOCUMENTS

| | | | | |
|---|---|---|---|---|
| 4,570,069 A | * | 2/1986 | Gager ................ | G01N 21/3577 250/301 |
| 4,699,509 A | * | 10/1987 | Kamiya ............... | G01N 21/255 356/436 |
| 5,049,742 A | * | 9/1991 | Hosonuma ......... | G01N 33/2888 250/301 |

(Continued)

FOREIGN PATENT DOCUMENTS

| | | |
|---|---|---|
| CN | 101287981 A | 10/2008 |
| CN | 101748562 A | 6/2010 |

(Continued)

OTHER PUBLICATIONS

Machine translation in English of JP 2005-273470.*
International Search Report dated May 22, 2018, issued for PCT/JP2018/005911.

*Primary Examiner* — Roy M Punnoose
(74) *Attorney, Agent, or Firm* — Locke Lord LLP

(57) ABSTRACT

An oil state detection device includes an index member, a lighting device that illuminates the index member, and a photographing device that photographs the index member through oil in a machine device.

10 Claims, 11 Drawing Sheets

(56) References Cited

U.S. PATENT DOCUMENTS

| | | | | |
|---|---|---|---|---|
| 5,572,320 | A | * | 11/1996 | Reintjes ............. G01N 15/0227 356/246 |
| 5,831,721 | A | * | 11/1998 | Alkafeef ............ G01N 15/0211 356/70 |
| 6,091,484 | A | * | 7/2000 | Venica ............... G01N 33/2888 356/301 |
| 6,151,108 | A | * | 11/2000 | Kwon ................. G01N 21/534 356/70 |
| 6,680,777 | B1 | * | 1/2004 | Wollert .............. F16H 57/0405 123/196 S |
| 7,126,677 | B2 | * | 10/2006 | Nakayama ............. F16C 17/24 356/70 |
| 7,764,360 | B2 | * | 7/2010 | Noguchi ............. G01N 21/85 356/70 |
| 9,046,502 | B2 | | 6/2015 | Chikamune |
| 9,201,054 | B2 | * | 12/2015 | Shirata .................. G01N 21/94 |
| 2005/0212533 | A1 | * | 9/2005 | Itomi ................ G01N 33/2888 324/698 |
| 2010/0220919 | A1 | | 9/2010 | Leclerc et al. |
| 2013/0250281 | A1 | * | 9/2013 | Shirata ............... G01N 21/8507 356/70 |
| 2016/0252448 | A1 | * | 9/2016 | Ida ....................... G01N 21/255 356/70 |
| 2016/0252490 | A1 | * | 9/2016 | Shirata ............... G01N 21/5907 356/70 |

FOREIGN PATENT DOCUMENTS

| | | | |
|---|---|---|---|
| CN | 104024829 A | 9/2014 | |
| EP | 2799839 A1 | 11/2014 | |
| JP | S62-53348 | 4/1987 | |
| JP | S64-10658 U | 1/1989 | |
| JP | H07-280792 A | 10/1995 | |
| JP | 2003-105806 A | 4/2003 | |
| JP | 2005-273470 | * 10/2005 | ............. F01M 11/12 |
| JP | 2009-25194 A | 2/2009 | |
| JP | 2010-281610 A | 12/2010 | |
| JP | 2012-173036 A | 9/2012 | |

* cited by examiner

OIL STATE DETECTION DEVICE, WORK MACHINE, MANAGEMENT SYSTEM, AND OIL STATE DETECTION METHOD

FIELD

The present invention relates to an oil state detection device, a work machine, a management system, and an oil state detection method.

BACKGROUND

Oil is used in a machine device. For example, a hydraulic oil is used or a lubricating oil is used in a hydraulic equipment. Also, a lubricating oil is used in an engine. A property of oil including at least one of the hydraulic oil and the lubricating oil is gradually deteriorated. A liquid property identification device used to determine a deterioration state of liquid is disclosed in Patent Literature 1.

CITATION LIST

Patent Literature

Patent Literature 1: Japanese Laid-open Patent Publication No. 2012-173036

SUMMARY

Technical Problem

When deteriorated oil is kept used, abrasion of a sliding part of a machine device is accelerated and a trouble such as a breakdown or damage of the machine device is generated, for example. In order to control generation of a trouble in a machine device, a technology with which a state of oil can be grasped accurately is demanded.

An aspect of the present invention is to provide an oil state detection device, a work machine, a management system, and an oil state detection method with which a state of oil can be grasped.

Solution to Problem

According to a first aspect of the present invention, an oil state detection device comprises: an index member; a lighting device that illuminates the index member; and a photographing device that photographs the index member through oil in a machine device.

According to a second aspect of the present invention, a work machine comprises: the oil state detection device according to the first aspect; and a determination unit that determines a state of the oil on the basis of image data acquired by the photographing device of the oil state detection device.

According to a third aspect of the present invention, a management system comprises: the oil state detection device according to the first aspect; and a determination unit that determines a state of the oil on the basis of image data acquired by the photographing device of the oil state detection device.

According to a fourth aspect of the present invention, an oil state detection method comprises: illuminating an index member through oil in a machine device; and photographing the index member through the oil.

Advantageous Effects of Invention

According to an aspect of the present invention, an oil state detection device, a work machine, a management system, and an oil state detection method with which a state of oil can be grasped is provided.

DESCRIPTION OF EMBODIMENTS

In the following, embodiments according to the present invention will be described with reference to the drawings. However, the present invention is not limited to these. Configuration elements of the embodiments described in the following can be arbitrarily combined. Also, there is a case where a part of the configuration elements is not used.

First Embodiment

[Work Machine and Management System]

Figure 1:
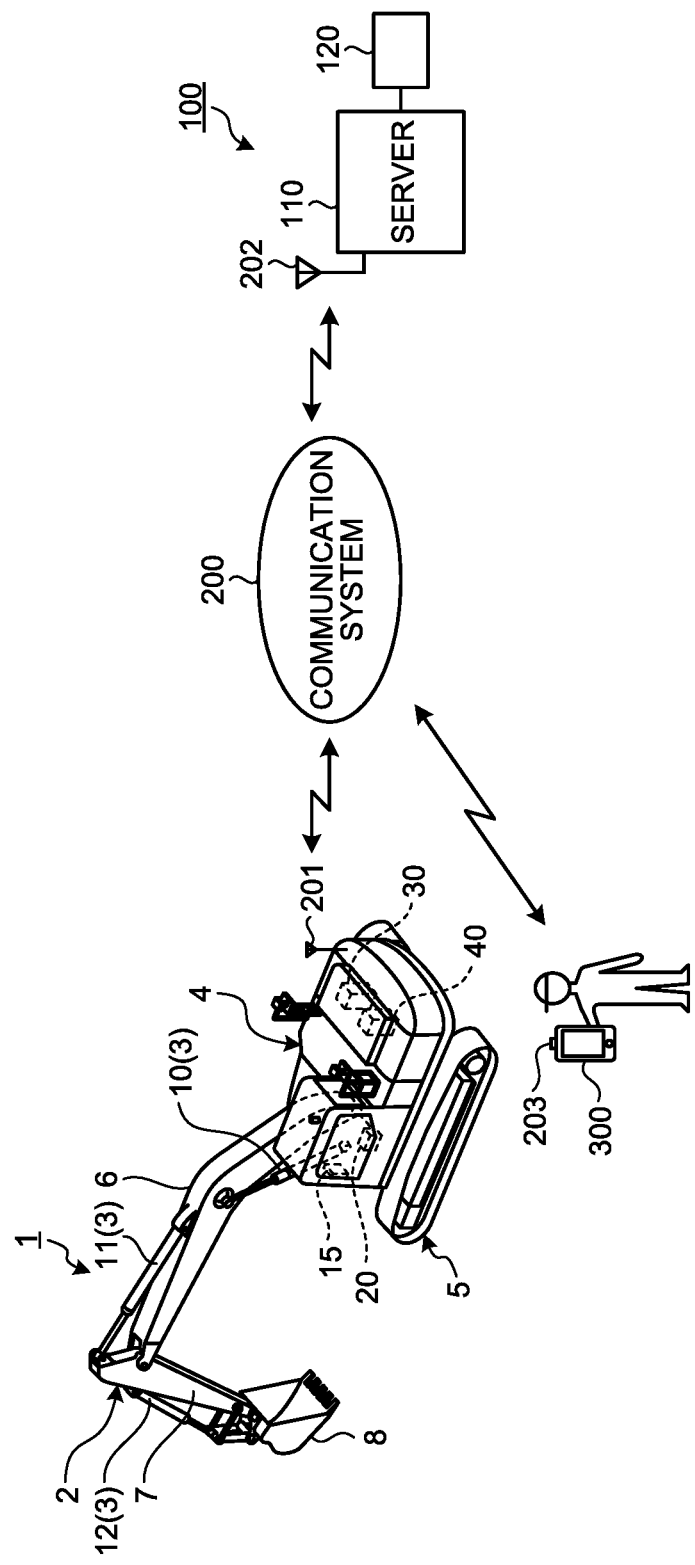
FIG. 1 is a view schematically illustrating one example of a work machine and a management system of the work machine according to a first embodiment.

FIG. 1 is a view schematically illustrating one example of a work machine 1 and a management system 100 of the work machine 1 according to the present embodiment. In the present embodiment, an example in which the work machine 1 is an excavator 1 will be described. In the following description, the work machine 1 will be arbitrarily referred to as the excavator 1.

The excavator 1 is in a workplace and works in the workplace. The management system 100 is in the workplace or a place distant from the workplace.

The excavator 1 includes a working equipment 2, a hydraulic cylinder 3 to drive the working equipment 2, a swinging body 4 to support the working equipment 2, a traveling body 5 to support the swinging body 4 in a swingable manner, a control device 20 including a computer system, a display device 15 arranged in an operating room, an engine 30 that is a power source of the excavator 1, and a hydraulic system 40 in which a hydraulic oil flows. The working equipment 2 is coupled to the swinging body 4. The traveling body 5 includes a crawler track. The excavator 1 travels by a rotation of the crawler track.

The working equipment 2 includes a boom 6 coupled to a swinging body 3, an arm 7 coupled to the boom 6, and a bucket 8 coupled to the arm 7.

The hydraulic cylinder 3 includes a boom cylinder 10 to drive the boom 6, an arm cylinder 11 to drive the arm 7, and a bucket cylinder 12 to drive the bucket 8.

The management system 100 manages an operating condition of the excavator 1, and a state of the hydraulic system 40 mounted in the excavator 1. The management system 100 manages one or a plurality of excavators 1. The plurality of excavators 1 may be in one workplace or may be in a plurality of different workplaces respectively. Note that one excavator 1 is illustrated as one example in FIG. 1.

Note that the management system 100 may manage a work machine of a kind different from the excavator 1. For example, a bulldozer or a wheel loader is exemplified as a work machine of a kind different from the excavator 1. The management system 100 may manage both of the bulldozer and the excavator 1, for example.

The management system 100 includes a server 110 including a computer system, and a display device 120 connected to the server 110.

The control device 20 of the excavator 1, the server 110 of the management system 100, and a communication terminal 300 communicate with each other through a communication system 200. The communication system 200 includes a wireless communication device 201 provided in the excavator 1, a wireless communication device 202 provided in the server 110, and a wireless communication device 203 provided in the communication terminal 300. The communication system 200 includes at least one of the Internet, a local area network (LAN), a mobile-phone communication network, and a satellite communication network.

The communication terminal 300 is a mobile device that can be held by a driver of the excavator 1, a worker working in a workplace, a supervisor of a workplace, or an administrator to perform maintenance and a checkout of the excavator 1. The communication terminal 300 includes a mobile computer system such as a smartphone or a tablet-type personal computer.

[Hydraulic System]

Figure 2:
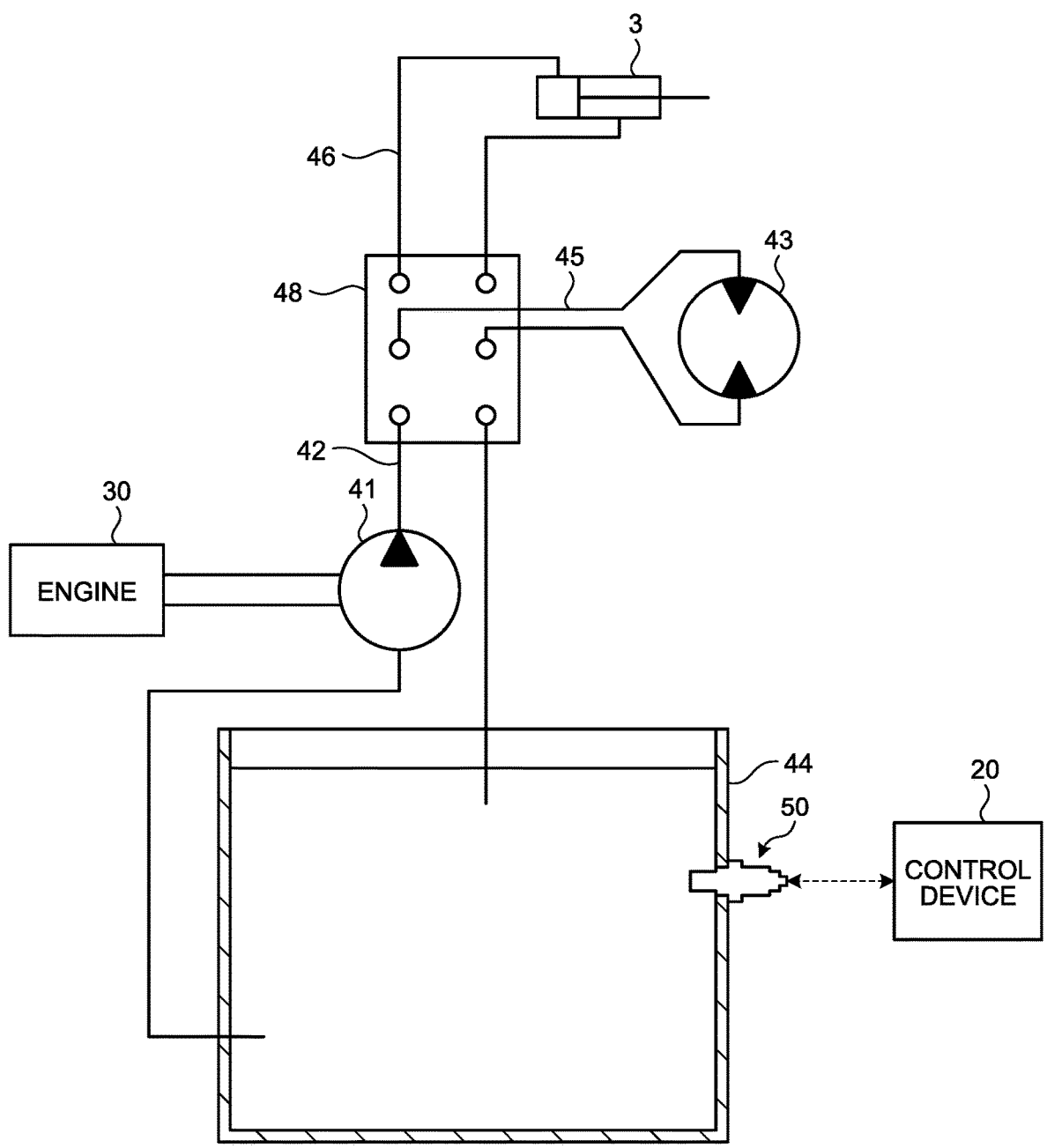
FIG. 2 is a view schematically illustrating one example of a hydraulic system according to the first embodiment.

FIG. 2 is a view schematically illustrating one example of the hydraulic system 40 according to the present embodiment. As illustrated in FIG. 2, the hydraulic system 40 includes a hydraulic pump 41 driven by power generated in the engine 30, a main valve 48 connected to the hydraulic pump 41 through a pipeline 42, a hydraulic motor 43 driven on the basis of a hydraulic oil supplied from the hydraulic pump 41 through the main valve 48, a hydraulic cylinder 3 driven on the basis of a hydraulic oil supplied from the hydraulic pump 41 through the main valve 48, and a hydraulic oil tank 44 that stores the hydraulic oil. Note that a hydraulic pump 41 that discharges a hydraulic oil supplied to the hydraulic motor 43, and a hydraulic pump 41 that discharges hydraulic oil supplied to the hydraulic cylinder 3 may be different hydraulic pumps. Note that a plurality of hydraulic motors 43 may be provided. The hydraulic motor 43 may be a swivel motor to make the swinging body 4 swing.

The engine 30 is a power source of the hydraulic pump 41. The engine 30 is, for example, a diesel engine.

The hydraulic pump 41 is a power source of the hydraulic motor 43 and a power source of the hydraulic cylinder 3. The hydraulic pump 41 is connected to an output shaft of the engine 30 and is driven by power generated in the engine 30. The hydraulic pump 41 sucks the hydraulic oil stored in the hydraulic oil tank 44 and performs a discharge from a discharge port. The hydraulic oil discharged from the hydraulic pump 41 is supplied to the hydraulic motor 43 through the main valve 48 and a pipeline 45. Also, the hydraulic oil discharged from the hydraulic pump 41 is supplied to the hydraulic cylinder 3 through the main valve 48 and a pipeline 46.

The hydraulic motor 43 is a power source of the traveling body 5. The traveling body 5 travels by power generated in the hydraulic motor 43. The hydraulic oil discharged from the hydraulic pump 41 flows into the hydraulic motor 43 through the main valve 48 and the pipeline 45. An output shaft of the hydraulic motor 43 rotates on the basis of the hydraulic oil. By the rotation of the output shaft of the hydraulic motor 43, the traveling body 5 connected to the output shaft of the hydraulic motor 43 travels. The hydraulic oil flowing out of the hydraulic motor 43 returns to the hydraulic oil tank 44 through the main valve 48.

The hydraulic cylinder 3 is a power source of the working equipment 2. The working equipment 2 operates by power generated in the hydraulic cylinder 3. The hydraulic oil discharged from the hydraulic pump 41 flows into the hydraulic cylinder 3 through the main valve 48 and the pipeline 46. The hydraulic cylinder 3 is extended/contracted on the basis of the hydraulic oil. By extraction/contraction of the hydraulic cylinder 3, the working equipment 2 coupled to the hydraulic cylinder 3 operates. The hydraulic oil discharged from the hydraulic cylinder 3 returns to the hydraulic oil tank 44 through the main valve 48.

[Oil State Detection Device]

Figure 3:
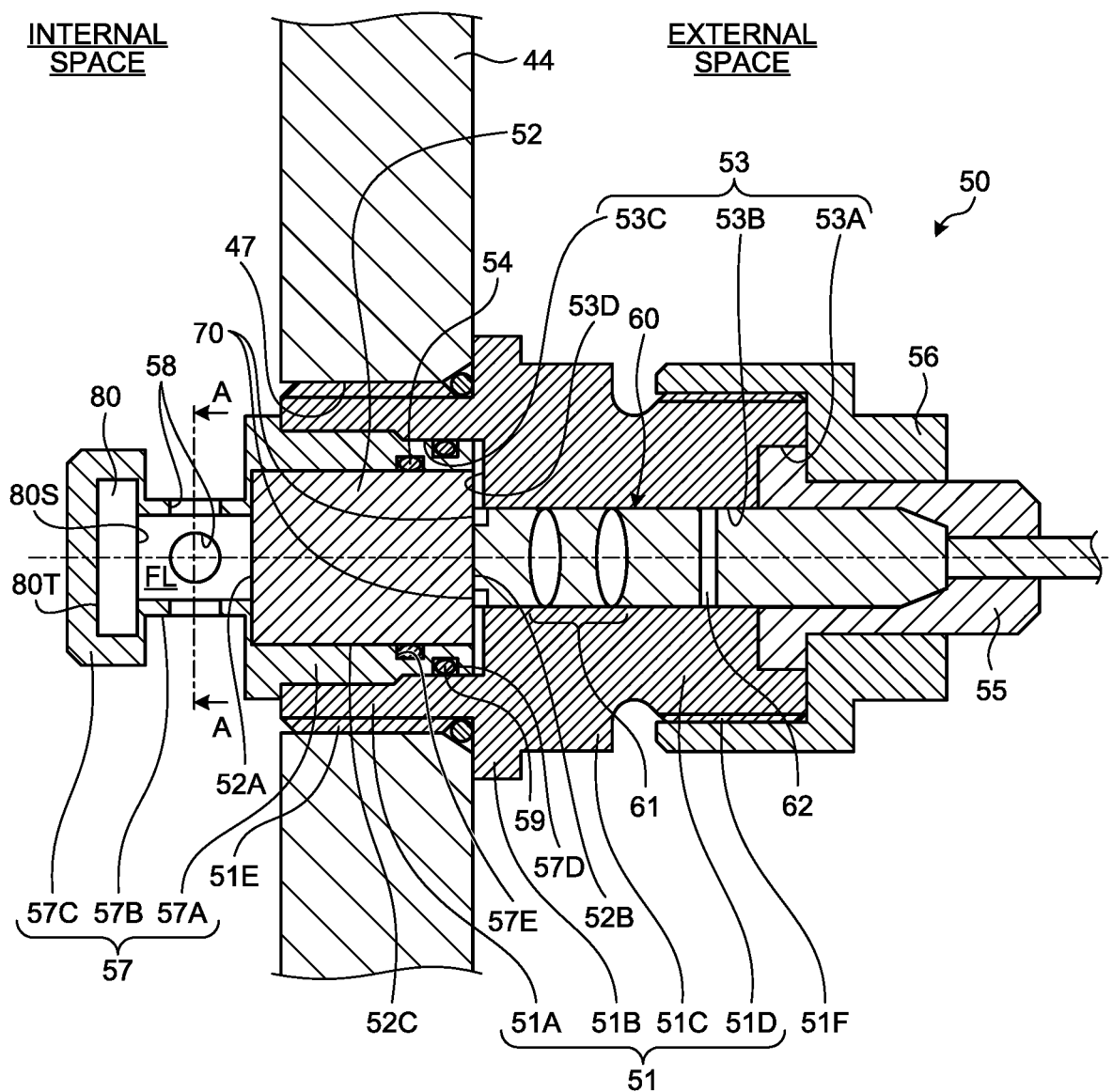
FIG. 3 is a sectional side view schematically illustrating one example of an oil state detection device according to the first embodiment.

FIG. 3 is a sectional side view schematically illustrating one example of a state detection device 50 according to the present embodiment. The state detection device 50 detects a state of a hydraulic oil of a hydraulic equipment. In the present embodiment, the hydraulic equipment includes at least one of the hydraulic pump 41, the hydraulic motor 43, the hydraulic cylinder 3, the hydraulic oil tank 44, the pipeline 42, the pipeline 45, and the pipeline 46. For example, as illustrated in FIG. 2, it is assumed in the following description that the state detection device 50 is attached to the hydraulic oil tank 44 and detects a state of a hydraulic oil stored in an internal space of the hydraulic oil tank 44.

As illustrated in FIG. 3, the state detection device 50 includes an index member 80, a lighting device 70 that illuminates the index member 80, and a photographing device 60 that photographs the index member 80 through the hydraulic oil in the hydraulic oil tank 44.

Also, the state detection device 50 includes a plug 51 that supports the photographing device 60, a spacer member 52 supported by the plug 51, a grommet 55 connected to the plug 51, a cap member 56 attached to the plug 51 and the grommet 55, and a holding member 57 coupled to the plug 51.

The plug 51 is a metallic cylindrical member. The plug 51 is detachably attached to at least a part of the hydraulic oil tank 44. In the present embodiment, the plug 51 is detachably arranged in an opening 47 that connects an internal space and an external space of the hydraulic oil tank 44. In the present embodiment, the opening 47 is provided in a side plate of the hydraulic oil tank 44. Note that the opening 47 may be provided in a bottom plate of the hydraulic oil tank 44.

The plug 51 includes a shaft part 51A arranged in the opening 47 in the hydraulic oil tank 44, a flange part 51B that is arranged next to the shaft part 51A in an axial direction of the plug 51 and that has a larger outside diameter than the shaft part 51A, a head part 51C that is arranged next to the flange part 51B in the axial direction of the plug 51 and that has a smaller outside diameter than the flange part 51B, and a cap attachment part 51D that is arranged next to the head part 51C in the axial direction of the plug 51 and that has a smaller outside diameter than the head part 51C.

The shaft part 51A is a part arranged in the opening 47 in the hydraulic oil tank 44. A screw thread 51E is provided on an outer surface of the shaft part 51A. A thread groove coupled with the screw thread 51E is provided in an inner surface of the opening 47 in the hydraulic oil tank 44. By coupling between the screw thread 51E on the shaft part 51A and the thread groove in the opening 47, the plug 51 is attached to the hydraulic oil tank 44. By release of the coupling between the screw thread 51E on the shaft part 51A and the thread groove in the opening 47, the plug 51 is detached from the hydraulic oil tank 44.

The flange part 51B is a part in contact with an outer surface of the side plate of the hydraulic oil tank 44. The flange part 51B is annular on a plane orthogonal to a central axis of the plug 51.

The head part 51C is a part operated with a tool when the plug 51 is attached to the hydraulic oil tank 44 or the plug 51 is detached from the hydraulic oil tank 44. An outer shape of the head part 51C is quadrangular or hexagonal on a plane orthogonal to the central axis of the plug 51.

The cap attachment part 51D is a part to which the cap member 56 is attached. A screw thread 51F is provided on an outer surface of the cap attachment part 51D. A thread groove coupled with the screw thread 51F is provided in an inner surface of the cap member 56. By coupling between the screw thread 51F on the cap attachment part 51D and the thread groove in the cap member 56, the cap member 56 is attached to the plug 51. By release of the coupling between the screw thread 51F on the cap attachment part 51D and the thread groove in the cap member 56, the cap member 56 is detached from the plug 51. A part of the cap member 56 is arranged around the cap attachment part 51D. A part of the cap member 56 is arranged around the grommet 55.

The plug 51 has an attachment hole 53 extended in the axial direction of the plug 51. The attachment hole 53 penetrates a leading end surface of the shaft part 51A and a base end surface of the cap attachment part 51D. The leading end surface of the shaft part 51A faces the internal space of the hydraulic oil tank 44. The base end surface of the cap attachment part 51D is arranged in the external space of the hydraulic oil tank 44.

The attachment hole 53 has a grommet fitting hole part 53A in which at least a part of the grommet 55 is arranged, a first housing hole part 53B that is arranged next to the grommet fitting hole part 53A in the axial direction of the plug 51 and that has a smaller inside diameter than the grommet fitting hole part 53A, and a second housing hole part 53C that is arranged next to the first housing hole part 53B in the axial direction of the plug 51 and that has a larger inside diameter than the first housing hole part 53B.

The grommet fitting hole part 53A is a part in which at least a part of the grommet 55 is arranged. An end part of the grommet fitting hole part 53A is connected to an opening provided in the base end surface of the cap attachment part 51D. The first housing hole part 53B is a part in which at least a part of the photographing device 60 is arranged. The second housing hole part 53C is a part in which at least a part of the spacer member 52 is arranged.

The spacer member 52 is a transparent member that can transmit visible light. The spacer member 52 is a columnar member arranged in the second housing hole part 53C. The spacer member 52 has a leading end surface 52A, a base end surface 52B facing an opposite direction of the leading end surface 52A, an outer peripheral surface 52C that connects an outer edge of the leading end surface 52A and an outer edge of the base end surface 52B.

The leading end surface 52A of the spacer member 52 faces the internal space of the hydraulic oil tank 44. The leading end surface 52A is in contact with the hydraulic oil stored in the hydraulic oil tank 44. An outer edge region in the base end surface 52B of the spacer member 52 is supported by a pressure-receiving surface 53D. A central region in the base end surface 52B of the spacer member 52 faces the photographing device 60.

The spacer member 52 has a heat-resistance property and an oil-resistance property. In the present embodiment, the spacer member 52 has a polycarbonate resin. Note that the spacer member 52 may be made of glass.

The spacer member 52 is arranged in a position closer to the internal space of the hydraulic oil tank 44 than the photographing device 60. The spacer member 52 is arranged in a boundary between the internal space and the external space of the hydraulic oil tank 44. The photographing device 60 is arranged in the external space of the hydraulic oil tank 44. The spacer member 52 protects the photographing device 60 from a pressure or contamination by the hydraulic oil in the internal space of the hydraulic oil tank 44.

The holding member 57 holds the index member 80. The holding member 57 holds the index member 80 in such a manner as to face the spacer member 52. In the present embodiment, the holding member 57 holds the index member 80 in such a manner that the leading end surface 52A of the spacer member 52 and a surface 80S of the index member 80 face each other via a gap.

The holding member 57 is coupled to the plug 51. The holding member 57 has a cylindrical part 57A arranged between an inner surface of the second housing hole part 53C of the plug 51 and the outer peripheral surface 52C of the spacer member 52, a flow channel part 57B arranged next to the cylindrical part 57A in the axial direction of the plug 51, and a holding part 57C arranged next to the flow channel part 57B in the axial direction of the plug 51.

The cylindrical part 57A is arranged around the outer peripheral surface 52C of the spacer member 52 in the second housing hole part 53C of the attachment hole 53. The cylindrical part 57A is sandwiched between the inner surface of the second housing hole part 53C and the outer peripheral surface 52C of the spacer member 52, whereby the holding member 57 is supported by the plug 51. In the present embodiment, an O ring-like sealing member 59 is provided between the inner surface of the second housing hole part 53C and an outer surface of the cylindrical part 57A. In the present embodiment, a seal groove 57D is provided in an outer peripheral surface of the cylindrical part 57A. The sealing member 59 is arranged in the seal groove 57D. Also, an O ring-like sealing member 54 is arranged between an inner peripheral surface of the cylindrical part 57A and the outer peripheral surface 52C of the spacer member 52. In the present embodiment, a seal groove 57E is provided in the inner peripheral surface of the cylindrical part 57A. The sealing member 54 is arranged in the seal groove 57E. By the sealing member 54 and the sealing member 59, intrusion of the hydraulic oil in the internal space of the hydraulic oil tank 44 into the photographing device 60 is controlled.

The holding part 57C holds the index member 80 in such a manner that the index member 80 and the spacer member 52 face each other via a gap. The surface 80S of the index member 80 held by the holding part 57C and the leading end surface 52A of the spacer member 52 supported by the plug 51 face each other via a gap.

The flow channel part 57B is arranged between the index member 80 held by the holding part 57C and the spacer member 52 supported by the plug 51. The flow channel part 57B couples the cylindrical part 57A and the holding part 57C. The flow channel part 57B is a cylindrical member. An opening 58 is provided in a part of the flow channel part 57B.

The flow channel part 57B, the holding part 57C, and the index member 80 held by the holding part 57C are arranged in the internal space of the hydraulic oil tank 44. The flow channel part 57B, the holding part 57C, and the index member 80 held by the holding part 57C are immersed in the hydraulic oil stored in the internal space of the hydraulic oil tank 44.

The photographing device 60 photographs the index member 80 through the hydraulic oil in the hydraulic oil tank 44. The photographing device 60 is supported by the plug 51. A part of the photographing device 60 is arranged in the first housing hole part 53B. A part of the photographing device 60 is attached to the grommet 55.

An optical path FL between the surface 80S of the index member 80 and the leading end surface 52A of the spacer member 52 is filled with the hydraulic oil. In the present embodiment, the photographing device 60 acquires image data of the index member 80 and image data of the hydraulic oil that fills the optical path FL. The photographing device 60 acquires the image data of the index member 80 and the image data of the hydraulic oil in the optical path FL through the spacer member 52. The image data acquired by the photographing device 60 is output to the control device 20.

The photographing device 60 includes an optical system 61, and an image sensor 62 that receives light through the optical system 61. The optical system 61 includes at least one collecting lens. The optical system 61 faces the base end surface 52B of the spacer member 52. The image sensor 62 includes a charge coupled device (CCD) image sensor or a complementary metal oxide semiconductor (CMOS) image sensor.

The lighting device 70 illuminates the surface 80S of the index member 80 through the hydraulic oil in the optical path FL and the spacer member 52. The lighting device 70 includes a light emitting diode (LED) and emits illumination light. The lighting device 70 faces the base end surface 52B of the spacer member 52. The lighting device 70 is arranged around an optical axis of the optical system 61. The lighting device 70 emits illumination light to the surface 80S of the index member 80 through the spacer member 52 and the hydraulic oil in the optical path FL.

The optical path FL is defined inside the flow channel part 57B. The optical path FL includes an optical path of the illumination light emitted from the lighting device 70 to the index member 80 and an optical path of reflection light of the illumination light reflected on the surface 80S of the index member 80. At least a part of the hydraulic oil stored in the internal space of the hydraulic oil tank 44 flows in the optical path FL between the index member 80 and the spacer member 52. The optical path FL is filled with the hydraulic oil.

Through the hydraulic oil, which fills the optical path FL, and a spacer member 51, the photographing device 60 photographs the index member 80 illuminated by the lighting device 70. With this arrangement, image data of the index member 80 and image data of the hydraulic oil in the optical path FL are acquired through the spacer member 52.

Figure 4:
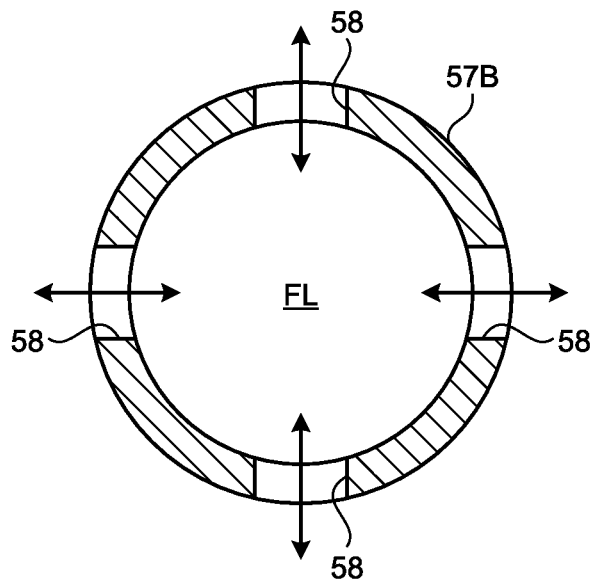
FIG. 4 is a sectional view illustrating one example of a flow channel part according to the first embodiment.

FIG. 4 is a sectional view illustrating one example of the flow channel part 57B according to the present embodiment. FIG. 4 is a sectional view of the flow channel part 57B on a plane orthogonal to an optical axis of the optical system 61 and corresponds to a cross-sectional arrow view taken along the line A-A in FIG. 3. As illustrated in FIG. 4, the flow channel part 57B is an annular member surrounding the optical path FL. The flow channel part 57B includes a plurality of openings 58. At least a part of the hydraulic oil stored in the hydraulic oil tank 44 flows into an inner side of the flow channel part 57B through the openings 58. With this arrangement, the optical path FL is filled with the hydraulic oil. Also, at least a part of the hydraulic oil that fills the optical path FL flows to an outer side of the flow channel part 57B through the openings 58. In the present embodiment, the flow channel part 57B is immersed in the hydraulic oil in the hydraulic oil tank 44, and the hydraulic oil runs in a space on an inner side of the flow channel part 57B including the optical path FL and a space on an outer side of the flow channel part 57B.

[Index Member]

Figure 5:
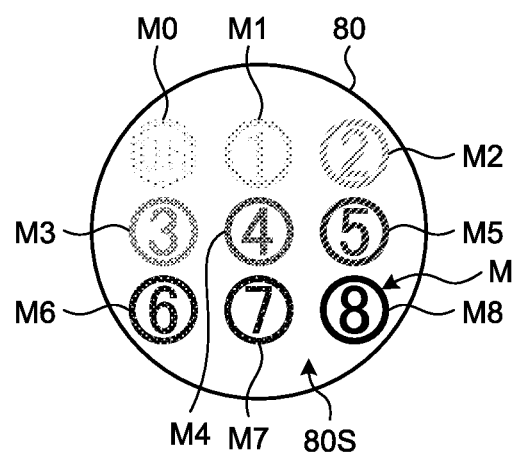
FIG. 5 is a view illustrating one example of an index member according to the first embodiment.

FIG. 5 is a view illustrating one example of the index member 80 according to the present embodiment. As illustrated in FIG. 4 and FIG. 5, the index member 80 is a plate-like member. The index member 80 has a heat-resistance property and an oil-resistance property. In the present embodiment, the index member 80 has a polyacetal resin.

The index member 80 has a surface 80S, and a rear surface 80T facing an opposite direction of the surface 80S. The surface 80S of the index member 80 is in contact with the hydraulic oil in the optical path FL. The rear surface 80T of the index member 80 faces the holding part 57C.

The index member 80 has a plurality of marks M for determination of transparency of the hydraulic oil. The plurality of marks M is provided on the surface 80S of the index member 80. The marks M are drawn on the surface 80S of the index member 80 with an oil-resistant ink.

In the present embodiment, the surface 80S of the index member 80 is white. The marks M are drawn with an oil-resistant ink in a hue different from white on the white surface 80S (base). In the present embodiment, each of the plurality of marks M has a hue identical or approximate to that of the hydraulic oil. A hue of the plurality of marks M is, for example, brown.

In the present embodiment, eight marks M are provided on the index member 80. In the present embodiment, the marks M have a design in which numbers "0.5," "1," "2," "3," "4," "5," "6," "7," and "8" are respectively surrounded by circles. In the following description, the mark M including "0.5" is arbitrarily referred to as a reference mark M0 in the following description. The mark M including "1" is arbitrarily referred to as a first mark M1. The mark M including "2" is arbitrarily referred to as a second mark M2. The mark M including "3" is arbitrarily referred to as a third mark M3. The mark M including "4" is arbitrarily referred to as a fourth mark M4. The mark M including "5" is arbitrarily referred to as a fifth mark M5. The mark M including "6" is arbitrarily referred to as a sixth mark M6. The mark M including "7" is arbitrarily referred to as a seventh mark M7. The mark M including "8" is arbitrarily referred to as an eighth mark M8.

Note that the marks M include numbers in the present embodiment. However, alphabets may be included instead of the numbers.

In the present embodiment, the plurality of marks M has different color density. In the present embodiment, density of the reference mark M0 is the lowest, density of the first mark M1 is low next to the reference mark M0, density of the second mark M2 is low next to the first mark M1, density of the third mark M3 is low next to the second mark M2, density of the fourth mark M4 is low next to the third mark M3, density of the fifth mark M5 is low next to the fourth mark M4, density of the sixth mark M6 is low next to the fifth mark M5, density of the seventh mark M7 is low next to the sixth mark M6, and density of the eighth mark M8 is the highest among the plurality of marks M.

Note that the plurality of marks M may have different luminosity. For example, luminosity may be in the following manner. That is, luminosity of the reference mark M0 is the highest, luminosity of the first mark M1 is high next to the reference mark M0, luminosity of the second mark M2 is high next to the first mark M1, luminosity of the third mark M3 is high next to the second mark M2, luminosity of the fourth mark M4 is high next to the third mark M3, luminosity of the fifth mark M5 is high next to the fourth mark M4, luminosity of the sixth mark M6 is high next to the fifth mark M5, luminosity of the seventh mark M7 is high next to the sixth mark M6, and luminosity of the eighth mark M8 is the lowest among the plurality of marks M.

Note that the plurality of marks M may have different chroma. For example, chroma may be in the following manner. That is, chroma of the reference mark M0 is the highest, chroma of the first mark M1 is high next to the reference mark M0, chroma of the second mark M2 is high next to the first mark M1, chroma of the third mark M3 is high next to the second mark M2, chroma of the fourth mark M4 is high next to the third mark M3, chroma of the fifth mark M5 is high next to the fourth mark M4, chroma of the sixth mark M6 is high next to the fifth mark M5, chroma of the seventh mark M7 is high next to the sixth mark M6, and chroma of the eighth mark M8 is the lowest among the plurality of marks M.

The marks M correspond to a color that changes depending on a deterioration state of the hydraulic oil. Also, the marks M may be prepared for each hydraulic oil manufacturer.

In the present embodiment, the plurality of marks M is arranged in parallel with intervals on the surface 80S of the index member 80. Each of the plurality of marks M is arranged in a visual field region of the optical system 61 of the photographing device 60.

Figure 6:
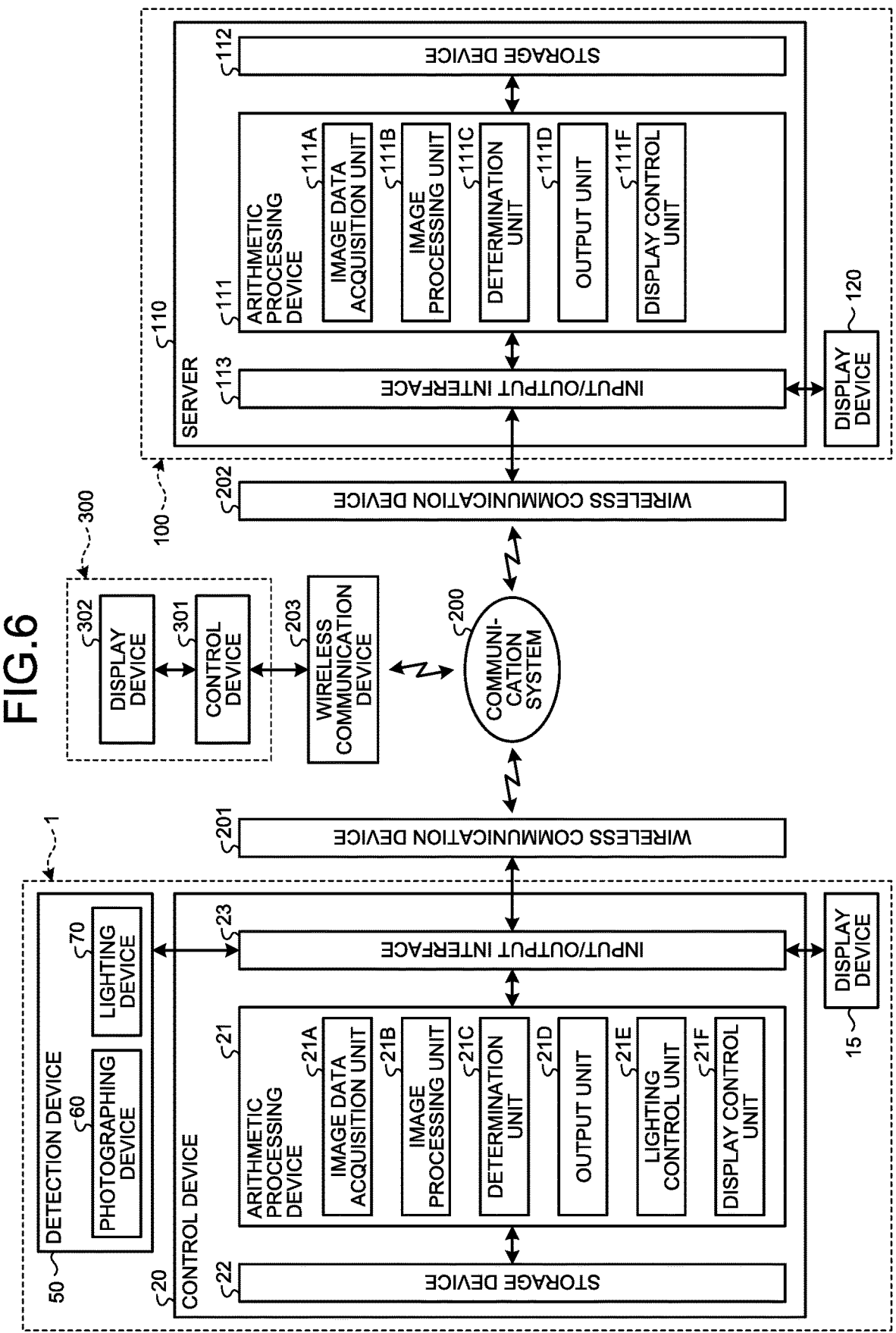
FIG. 6 is a functional block diagram illustrating a work machine, a server, and a communication terminal according to the first embodiment.

[Control device, server, and communication terminal]
FIG. 6 is a functional block diagram illustrating the excavator 1, the server 110, and the communication terminal 300 according to the present embodiment.

The control device 20 includes a computer system mounted in the excavator 1. The control device 20 includes an arithmetic processing device 21 including a processor such as a central processing unit (CPU), a storage device 22 including a non-volatile memory such as a random access memory (RAM) and a volatile memory such as a read only memory (ROM), and an input/output interface 23.

The arithmetic processing device 21 includes an image data acquisition unit 21A, an image processing unit 21B, a determination unit 21C, an output unit 21D, a lighting control unit 21E, and a display control unit 21F.

The image data acquisition unit 21A acquires image data, which is acquired by the photographing device 60, from the photographing device 60 by wire, air, or a controller area network (CAN). The image processing unit 21B performs image processing of the image data acquired by the image data acquisition unit 21A.

The determination unit 21C determines a state of the hydraulic oil on the basis of the image data which is acquired by the image data acquisition unit 21A and on which the image processing is performed by the image processing unit 21B.

The output unit 21D outputs the image data acquired by the image data acquisition unit 21A, the image data on which the image processing is performed by the image processing unit 21B, and determination data indicating a result of the determination by the determination unit 21C to the server 110 through the input/output interface 23 and the communication system 200.

The lighting control unit 21E outputs a control signal to control the lighting device 70 provided in the state detection device 50.

The display control unit 21F outputs display data to be displayed on the display device 15 provided in the excavator 1. The display device 15 includes a flat panel display such as a liquid crystal display (LCD) or an organic electroluminescence display (OELD). The display data includes at least one of the image data acquired by the image data acquisition unit 21A, the image data on which the image processing is performed by the image processing unit 21B, and the determination data indicating a result of the determination by the determination unit 21C.

The server 110 includes a computer system. The server 110 includes an arithmetic processing device 111 including a processor such as a central processing unit (CPU), a storage device 112 including a non-volatile memory such as a random access memory (RAM) and a volatile memory such as a read only memory (ROM), and an input/output interface 113.

The arithmetic processing device 111 includes an image data acquisition unit 111A, an image processing unit 111B, a determination unit 111C, an output unit 111D, and a display control unit 111F.

The image data acquisition unit 111A acquires image data acquired by the photographing device 60 and transmitted from the excavator 1 through the communication system 200. The image processing unit 111B performs image processing of the image data acquired by the image data acquisition unit 111A.

The determination unit 111C determines a state of the hydraulic oil on the basis of the image data which is acquired by the image data acquisition unit 111A and on which the image processing is performed by the image processing unit 111B.

The output unit 111D outputs the image data acquired by the image data acquisition unit 111A, the image data on which the image processing is performed by the image processing unit 111B, and determination data indicating a result of the determination by the determination unit 111C to at least one of the excavator 1 and the communication terminal 300 through the input/output interface 113 and the communication system 200.

The display control unit 111F outputs display data to be displayed on the display device 120 connected to the server 110. The display device 120 includes a flat panel display such as a liquid crystal display (LCD) or an organic electroluminescence display (OELD). The display data includes at least one of the image data acquired by the image data acquisition unit 111A, the image data on which the image processing is performed by the image processing unit 111B, and the determination data indicating a result of the determination by the determination unit 111C.

The communication terminal 300 includes a control device 301 including a computer system, and a display device 302 including a flat panel display. The control device 301 acquires the image data and the determination data output from the output unit 111D of the server 110. The image data output from the output unit 111D includes at least one of image data which is acquired by the image data acquisition unit 111A and on which image processing is not performed by the image processing unit 111B yet, and image data on which the image processing is performed by the image processing unit 111B. The control device 301 makes display data, which includes at least one of the image data and the determination data, displayed on the display device 302.

[Operation]

Figure 7:
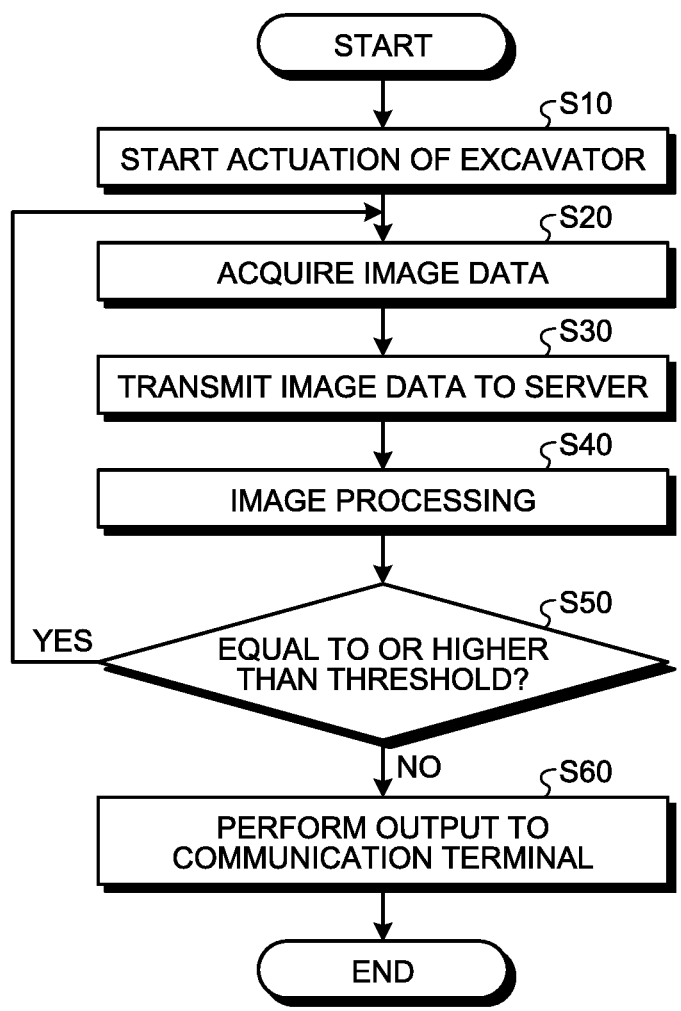
FIG. 7 is a flowchart illustrating one example of an operation of an excavator and a management system according to the first embodiment.

FIG. 7 is a flowchart illustrating one example of an operation of the excavator 1 and the management system 100 according to the present embodiment.

At a start of work in a workplace, a driver riding on the excavator 1 operates a key switch provided in the excavator 1. By key-on, driving of the engine 30 is started and actuation of the excavator 1 is started (Step S10).

The lighting device 70 of the state detection device 50 illuminates the index member 80 through the hydraulic oil filling the optical path FL. The photographing device 70 of the state detection device 50 photographs the index member 80 through the hydraulic oil filling the optical path FL. With this arrangement, image data of the index member 80 including the marks M is acquired by the photographing device 60 (Step S20).

The image data acquired by the photographing device 60 is acquired by the image data acquisition unit 21A of the control device 20. The output unit 21D of the control device 20 transmits the image data acquired by the image data acquisition unit 21A to the server 110 through the communication system 200 (Step S30).

The image data acquisition unit 111A of the server 110 acquires the image data transmitted from the control device 20. The image processing unit 111B of the server 110 performs image processing of the image data acquired by the image data acquisition unit 111A (Step S40).

The determination unit 111C determines a state of the hydraulic oil stored in the hydraulic oil tank 44 on the basis of the image data acquired by the photographing device 60. In the present embodiment, the determination unit 111C determines whether transparency of the hydraulic oil is equal to or higher than a threshold on the basis of the image data (Step S50).

The threshold with respect to the transparency of the hydraulic oil is a predetermined value and is stored in the storage device 112. The transparency of the hydraulic oil being equal to or higher than the threshold means that the hydraulic oil has high transparency and deterioration in the hydraulic oil is not progressed. The transparency of the hydraulic oil being lower than the threshold means that the hydraulic oil is cloudy, the transparency of the hydraulic oil is decreased, and deterioration in the hydraulic oil is progressed.

Note that a plurality of thresholds may be set. When the plurality of thresholds is set, the determination unit 111C can determine not only whether the hydraulic oil is dirty but also a degree (level) of dirtiness.

Figure 8:
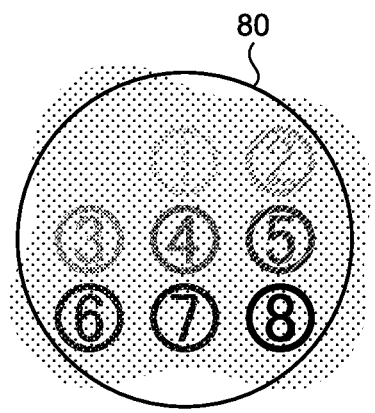
FIG. 8 is a view schematically illustrating one example of image data acquired by a photographing device according to the first embodiment.
Figure 9:
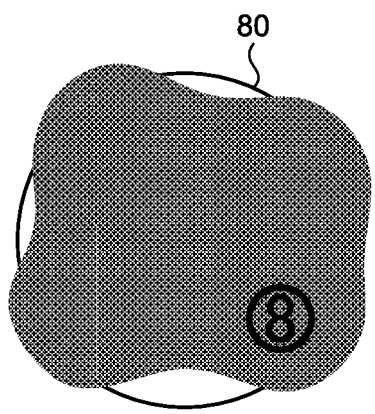
FIG. 9 is a view schematically illustrating one example of image data acquired by the photographing device according to the first embodiment.

Each of FIG. 8 and FIG. 9 is a view schematically illustrating one example of image data acquired by the photographing device 60 according to the present embodiment. FIG. 8 is a view illustrating one example of image data of when deterioration in a hydraulic oil is not progressed. FIG. 9 is a view illustrating one example of image data of when deterioration in a hydraulic oil is progressed.

In the present embodiment, the determination unit 111C determines a state of a hydraulic oil on the basis of image data of the marks M which data is acquired by the photographing device 60 As described above, the plurality of marks M is drawn in different color density on the surface 80S of the index member 80.

As illustrated in FIG. 8, when deterioration in a hydraulic oil is not progressed and transparency of the hydraulic oil is high, the photographing device 60 can acquire image data of a mark M even in a case where density (luminosity) of the mark M is low. In the example illustrated in FIG. 8, transparency of the hydraulic oil is high and the photographing device 60 can acquire image data of each of the first mark M1 to the eighth mark M8.

On the one hand, as illustrated in FIG. 9, when deterioration in a hydraulic oil is progressed and transparency of the hydraulic oil is low, it is difficult for the photographing device 60 to visually recognize an image of a mark M in a case where density (luminosity) of the mark M is low. In the example illustrated in FIG. 9, transparency of the hydraulic oil is low, and the photographing device 60 cannot acquire image data of the reference mark M0 to the seventh mark M7 although image data of the eighth mark M8 can be acquired.

In such a manner, a progress state in deterioration in the hydraulic oil and transparency of the hydraulic oil correspond to each other, and the transparency of the hydraulic oil and a mark M image data of which can be acquired correspond to each other. Thus, the determination unit 111C can determine transparency of the hydraulic oil on the basis of image data of the marks M which data is acquired by the photographing device 60.

In the present embodiment, it is assumed as one example that a threshold with respect to transparency of the hydraulic oil is transparency with which the image data of the seventh mark M7 can be acquired.

In a case where it is determined in Step S50 that the transparency of the hydraulic oil is equal to or higher than the threshold (Step S50: Yes), the processing goes back to the processing in Step S20. In the present embodiment, in a case where at least the image data of the seventh mark M7 is acquired, the determination unit 111C determines that the transparency of the hydraulic oil is equal to or higher than the threshold.

In a case where it is determined in Step S50 that the transparency of the hydraulic oil is not equal to or higher than the threshold (Step S50: No), the output unit 111D outputs determination data indicating a result of the determination by the determination unit 111C to the communication terminal 300 through the communication system 200 (Step S60). In the present embodiment, in a case where image data of the reference mark M0 to the seventh mark M7 is not acquired, the determination unit 111C determines that the transparency of the hydraulic oil is lower than the threshold.

In the communication terminal 300, display data indicating that the transparency of the hydraulic oil is lower than the threshold and deterioration in the hydraulic oil is progressed is displayed on the display device 302. With this arrangement, an administrator who holds the communication terminal 300 can grasp a state of the hydraulic oil in the hydraulic system 40 of the excavator 1 by looking at the display data displayed on the display device 302. The administrator can take measures such as performance of work of changing the hydraulic oil.

After the hydraulic oil is changed, the photographing device 60 of the state detection device 50 photographs the index member 80 through the changed hydraulic oil. Image data acquired by the photographing device 60 is transmitted to the server 110. On the basis of the image data acquired by the photographing device 60, the server 110 can acquire change history data indicating that the hydraulic oil is changed. The change history data is stored in the storage device 112.

[Effect]

As described above, a state detection device 50 including an index member 80, a lighting device 70 that illuminates the index member 80, and a photographing device 60 that photographs the index member 80 through a hydraulic oil in a hydraulic oil tank 44 that is one kind of a hydraulic equipment is provided according to the present embodiment. With this arrangement, it is possible to grasp a state of a hydraulic oil.

For example, in a case where a state of a hydraulic oil is visually determined, it is necessary to detach a plug provided in the hydraulic oil tank 44. In a case where a state of the hydraulic oil is visually determined periodically, work to detach the plug provided in the hydraulic oil tank 44 is generated each time. As a result, work efficiency is significantly decreased since it is necessary to stop the working equipment 2. Also, in visual determination of a state of the hydraulic oil, it is likely that a variation is generated in a determination result and that it becomes difficult to accurately grasp the state of the hydraulic oil.

According to the present embodiment, it becomes unnecessary to visually recognize a state of a hydraulic oil since the state detection device 50 is provided, and it is possible to accurately and efficiently grasp the state of the hydraulic oil at arbitrary timing.

Also, according to the present embodiment, since image data of a hydraulic oil is acquired, it is possible to grasp not only a deterioration state of the hydraulic oil but also existence/non-existence of a bubble in the hydraulic oil on the basis of the image data of the hydraulic oil.

Also, according to the present embodiment, a plurality of marks M for determination of transparency of a hydraulic oil is provided on the index member 80. By acquiring image data of the marks M, it is possible to determine transparency of the hydraulic oil according to a degree of appearance of the marks M. Thus, it is possible to grasp a deterioration state of the hydraulic oil quantitatively.

Also, according to the present embodiment, a plurality of marks M is provided on the surface 80S of the index member 80 in such a manner that at least one of color density, luminosity, and chroma thereof is different from each other. With this arrangement, it is possible to accurately determine transparency of a hydraulic oil according to a degree of appearance of the marks M.

Also, in the present embodiment, the photographing device 60 and the spacer member 52 are supported by the plug 51, and the index member 80 is immersed in the hydraulic oil stored in the internal space of the hydraulic oil tank 44. The photographing device 60 photographs the index member 80 immersed in the hydraulic oil through the hydraulic oil and the spacer member 52. With this arrangement, the photographing device 60 can acquire image data of the surface 80S of the index member 80, which is in contact with the hydraulic oil, in a state of being protected by the spacer member 52 from the hydraulic oil. It is possible to accurately determine transparency of the hydraulic oil on the basis of the image data of the surface 80S of the index member 80 in contact with the hydraulic oil.

Also, according to the present embodiment, the holding member 57 that holds the index member 80 is coupled to the plug 51. With this arrangement, a variation in a relative position between an index member 50 and the photographing device 60 supported by the plug 51 is controlled. The index member 80 and the spacer member 52 face each other via a gap. With this arrangement, the photographing device 60 can acquire image data of the index member 80 through the spacer member 52.

Also, in the present embodiment, the photographing device 60 supported by the plug 51 is arranged in the external space of the hydraulic oil tank 44. With this arrangement, a contact between the photographing device 60 and the hydraulic oil is controlled.

Second Embodiment

The second embodiment will be described. In the following description, the same sign is assigned to a configuration element identical or equivalent to that of the above-described embodiment, and a description thereof is simplified or omitted.

In the present embodiment, a lighting device 70 illuminates an index member 80 with a plurality of pieces of different colored light. In the present embodiment, no mark is provided on the index member 80. A surface 80S of the index member 80 is blank. A color of the surface 80S is white.

The lighting device 70 can illuminate the index member 80, for example, with red light, blue light, and green light. A lighting control unit 21E controls the lighting device 70 in such a manner that the index member 80 is illuminated with specific colored light.

An image sensor 62 receives reflection light of colored light reflected on the index member 80. When red light is emitted from the lighting device 70, the image sensor 62 receives reflection light of the red light emitted to the index member 80. When green light is emitted from the lighting device 70, a photographing device 60 receives reflection light of the green light emitted to the index member 80. When blue light is emitted from the lighting device 70, the photographing device 60 receives reflection light of the blue light emitted to the index member 80.

Image data (light reception data) of the reflection light which data is acquired by the photographing device 60 is transmitted to a server 110. A determination unit 111C of the server 110 determines a state of a hydraulic oil on the basis of the reflection light received by the photographing device 60. The image data (light reception data) of the reflection light which data is acquired in the photographing device 60 includes intensity of reflection light of colored light reflected on the surface 80S of the index member 80.

Figure 10:
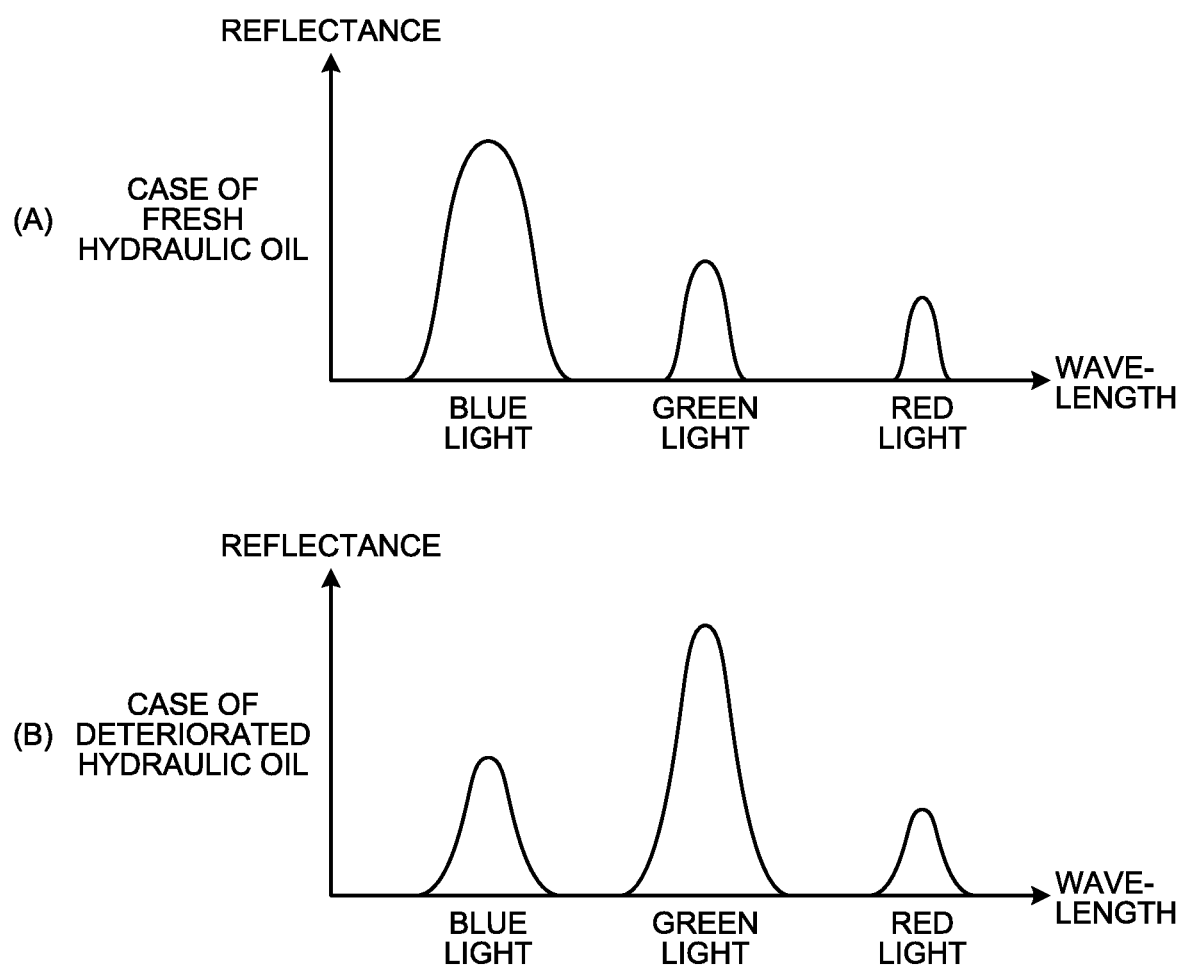
FIG. 10 is a view for describing a hydraulic oil state detection method by an oil state detection device according to a second embodiment.

FIG. 10 is a view for describing a hydraulic oil state detection method by a state detection device 50 according to the present embodiment. In a graph illustrated in FIG. 10, a horizontal axis indicates a wavelength of reflection light received by the photographing device 60. A vertical axis indicates reflectance indicating a ratio between intensity of colored light emitted to the surface 80S of the index member 80 and intensity of reflection light of the colored light reflected on the surface 80S. The intensity of colored light emitted to the surface 80S is a known value controlled by the lighting control unit 21E. The intensity of reflection light of the colored light reflected on the surface 80S is a value detected by the photographing device 60.

Reflectance of each piece of colored light varies depending on transparency of a hydraulic oil. When colored light is emitted through a fresh hydraulic oil (hydraulic oil having high transparency), reflectance of each piece of colored light is in a manner illustrated in FIG. 10(A). On the one hand, when colored light is emitted through a deteriorated hydraulic oil (hydraulic oil having low transparency), reflectance of each piece of colored light is in a manner illustrated in FIG. 10(B). In such a manner, reflectance characteristics of a plurality of pieces of colored light vary according to transparency of the hydraulic oil.

Correlation data indicating a relationship between transparency of a hydraulic oil and a reflectance characteristic of colored light is stored in a storage device 112. The correlation data includes so-called table data. The determination unit 111C calculates reflectance of colored light on the basis of intensity of reflection light which intensity is acquired by the photographing device 60 and intensity of colored light emitted to the surface 80S which intensity is derived from a control signal from the lighting control unit 21E. The determination unit 111C determines transparency of the hydraulic oil on the basis of the calculated reflectance of colored light and the correlation data stored in the storage device 112.

As described above, according to the present embodiment, it is possible to grasp a state of a hydraulic oil on the basis of a reflectance characteristic of each piece of colored light. According to the present embodiment, it is not necessary to provide a mark on the index member 80.

Third Embodiment

The third embodiment will be described. In the following description, the same sign is assigned to a configuration element identical or equivalent to that of the above-described embodiment, and a description thereof is simplified or omitted.

Figure 11:
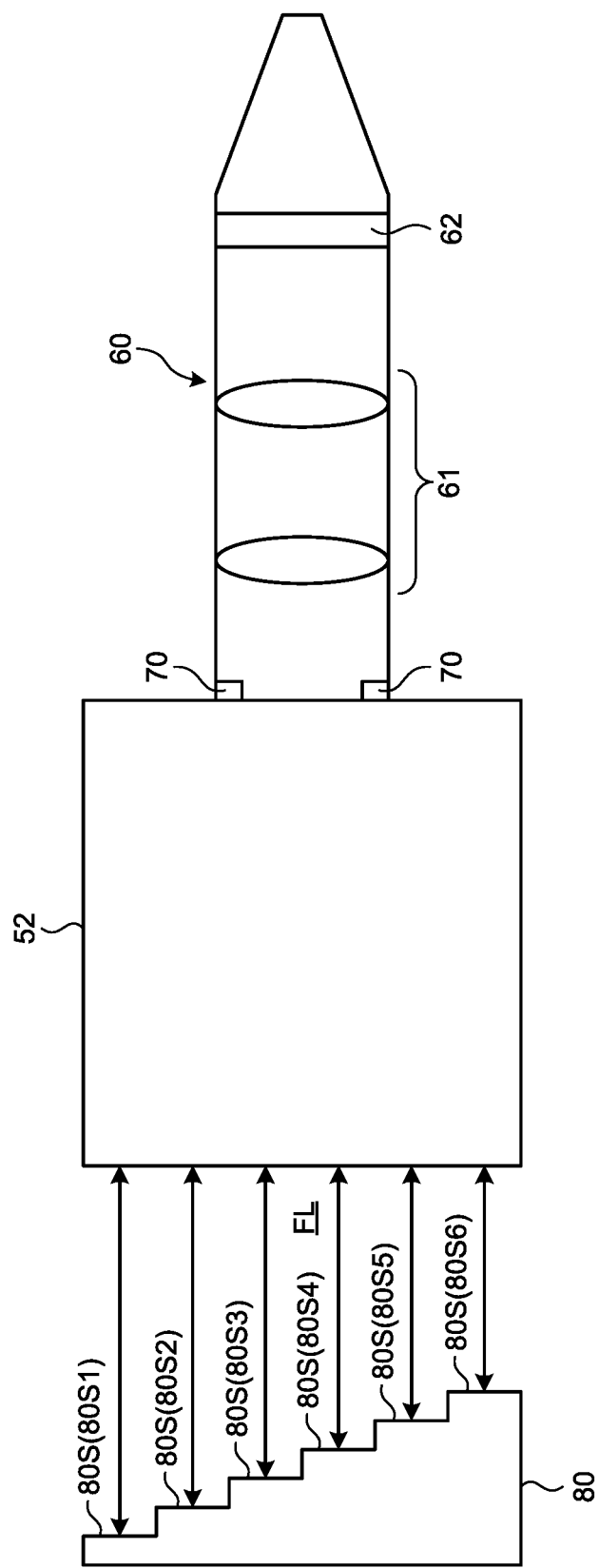
FIG. 11 is a view for describing a hydraulic oil state detection method by an oil state detection device according to a third embodiment.

FIG. 11 is a view for describing a hydraulic oil state detection method by a state detection device 50 according to the present embodiment. In the present embodiment, a photographing device 60 photographs a surface 80S of an index member 80 arranged in each of a plurality of positions at different distances from the photographing device 60. In the present embodiment, the index member 80 has a surface 80S arranged in each of a plurality of positions at different distances from the photographing device 60 in a direction in parallel with an optical axis of an optical system 61 of the photographing device 60. In the present embodiment, the surface 80S has a surface 80S1 having the longest distance to an imaging device 60, a surface 80S2 having a long distance to the imaging device 60 next to the surface 80S1, a surface 80S3 having a long distance to the imaging device 60 next to the surface 80S2, a surface 80S4 having a long distance to the imaging device 60 next to the surface 80S3, a surface 80S5 having a long distance to the imaging device 60 next to the surface 80S4, and a surface 80S6 having the shortest distance to the imaging device 60.

In the present embodiment, no mark is provided on the surface 80S of the index member 80. Note that marks M with identical hue, luminosity, and chroma may be respectively provided on the plurality of surfaces 80S.

The photographing device 60 acquires image data of the plurality of surfaces 80S through a hydraulic oil. The image data acquired by the photographing device 60 is transmitted to a server 110.

A determination unit 111C of the server 110 determines a state of the hydraulic oil on the basis of the image data of the surfaces 80S of the index member 80 which surfaces are respectively arranged in the plurality of positions. In a case where deterioration in the hydraulic oil is not progressed and transparency of the hydraulic oil is high, the photographing device 60 can acquire image data of the surface 80S1 having the longest distance to the photographing device 60. On the one hand, in a case where deterioration in the hydraulic oil is progressed and transparency of the hydraulic oil is low, the photographing device 60 cannot acquire image data of the surface 80S1 having the longest distance to the photographing device 60. As the transparency of the hydraulic oil becomes low, the surface 80S image data of which can be acquired by the photographing device 60 serially changes to the surface 80S2, the surface 80S3, the surface 80S4, the surface 80S5, and the surface 80S6. Thus, the determination unit 111C can determine a state of the hydraulic oil on the basis of the image data of the plurality of surfaces 80S which data is acquired by the photographing device 60.

As described above, it is possible to grasp a state of a hydraulic oil on the basis of a distance to a surface 80S image data of which can be acquired.

Note that it is assumed in the present embodiment that one index member 80 includes a plurality of surfaces 80S at different distances from the photographing device 60. That is, it is assumed that the index member 80 has a stepped surface 80S. A moving device that can move an index member 80 in a direction in parallel with an optical axis of an optical system 61 may be provided, and a distance between the index member 80 and a photographing device 60 may be adjusted by movement of the index member 80 by the moving device.

Fourth Embodiment

The fourth embodiment will be described. In the following description, the same sign is assigned to a configuration element identical or equivalent to that of the above-described embodiment, and a description thereof is simplified or omitted.

Figure 12:
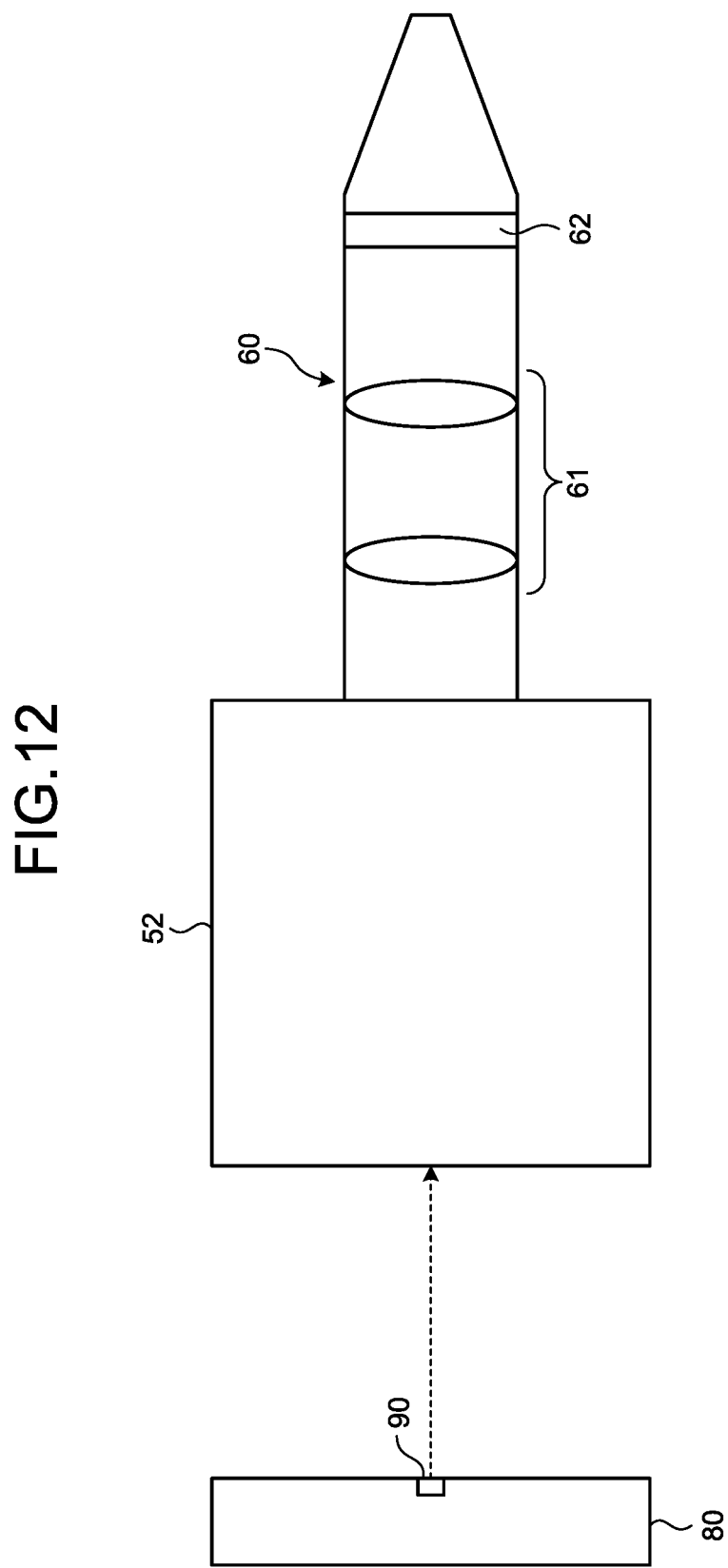
FIG. 12 is a view for describing a hydraulic oil state detection method by an oil state detection device according to a fourth embodiment.

FIG. 12 is a view for describing a hydraulic oil state detection method by a state detection device 50 according to the present embodiment. In the present embodiment, a lighting device 90 is provided in an index member 80. The lighting device 90 emits illumination light toward a photographing device 60. The lighting device 90 can adjust intensity of the emitted illumination light.

The illumination light emitted from the lighting device 90 illuminates the photographing device 60 through a hydraulic oil and a spacer member 52.

Image data (light reception data) of the illumination light which data is acquired by the photographing device 60 is transmitted to a server 110. A determination unit 111C of the server 110 determines a state of the hydraulic oil on the basis of the illumination light received by the photographing device 60. The image data (light reception data) of the illumination light which data is acquired by the photographing device 60 includes intensity of the illumination light emitted from the lighting device 90 provided in the index member 80.

The lighting device 90 emits illumination light with a plurality of different degrees of intensity. Intensity of the illumination light received by the photographing device 60 varies depending on transparency of the hydraulic oil. When illumination light is emitted through a fresh hydraulic oil (hydraulic oil having high transparency), the photographing device 60 can receive the illumination light even in a case where intensity of the illumination light is low. On the one hand, when illumination light is emitted through a deteriorated hydraulic oil (hydraulic oil having low transparency), illumination light with low intensity is not received by the photographing device 60. In such a manner, it is determined whether pieces of illumination light with a plurality of degrees of intensity are received by the photographing device 60 according to transparency of the hydraulic oil.

Image data (light reception data) of the illumination light which data is acquired by the photographing device 60 is transmitted to a server 110. A determination unit 111C of the server 110 determines a state of the hydraulic oil on the basis of the illumination light received by the photographing device 60.

As described above, it is possible to receive, by the photographing device 60, illumination light with a plurality of different degrees of intensity which light is emitted from the lighting device 90 immersed in a hydraulic oil, and to grasp a state of the hydraulic oil on the basis of whether the illumination light with the plurality of degrees of intensity is received.

Note that it is assumed in the present embodiment that one lighting device 90 is provided in the index member 80 and intensity of illumination light emitted from the one lighting device 90 is adjusted. A plurality of lighting devices 90 may be provided in an index member 80. Intensity of pieces of illumination light respectively emitted from these plurality of lighting devices 90 may be different from each other. The plurality of lighting devices 90 serially emit illumination light. The photographing device 60 serially receives the pieces of illumination light respectively emitted from the plurality of lighting devices 90. The determination unit 111C can determine a state of the hydraulic oil on the basis of light reception data of the photographing device 60.

Note that it is assumed in each of the above-described embodiments that a state detection device 50 is attached to a hydraulic oil tank 44. However, the state detection device 50 may be attached to at least one of a hydraulic pump 41, a hydraulic motor 43, a hydraulic cylinder 3, a pipeline 42, a pipeline 45, and a pipeline 46. A state detection device 50 may detect a state of a hydraulic oil in an internal space of the hydraulic pump 41, may detect a state of a hydraulic oil in an internal space of the hydraulic motor 43, may detect a state of a hydraulic oil in an internal space of the hydraulic cylinder 3, may detect a state of a hydraulic oil in an internal space of the pipeline 42, may detect a state of a hydraulic oil in an internal space of the pipeline 45, or may detect a state of a hydraulic oil in an internal space of the pipeline 46.

Fifth Embodiment

The fifth embodiment will be described. In the following description, the same sign is assigned to a configuration element identical or equivalent to that of the above-described embodiment, and a description thereof is simplified or omitted.

In each of the above-described embodiments, it is assumed that a state detection device 50 detects a state of a hydraulic oil in a hydraulic equipment that is one kind of a machine device. The state detection device 50 may detect a state of oil in a machine device different from a hydraulic equipment mounted in an excavator 1. For example, a state of a lubricating oil used in an engine 30 that is one kind of a machine device may be detected by the state detection device 50.

Figure 13:
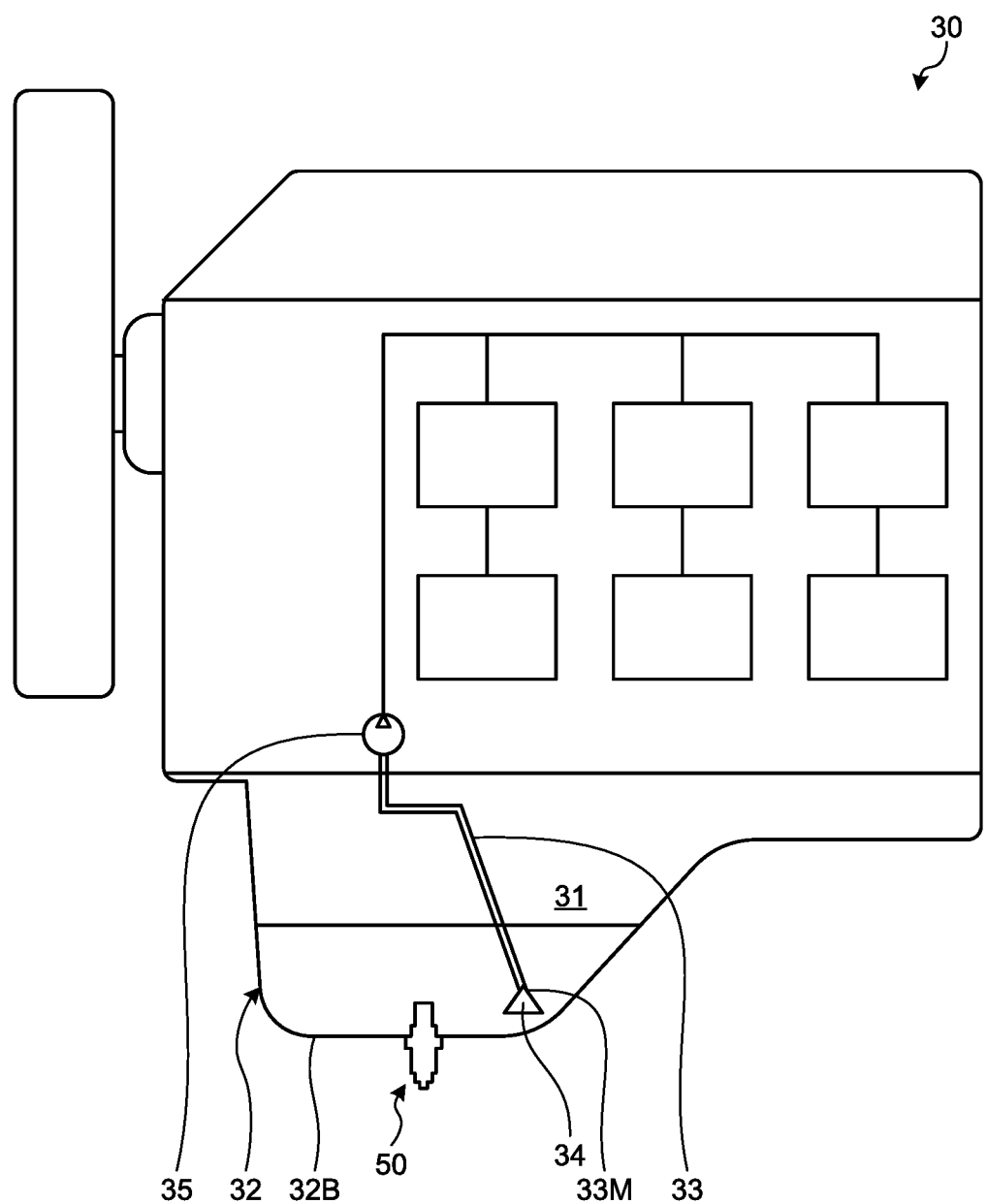
FIG. 13 is a view schematically illustrating one example of an oil state detection device provided in an engine according to a fifth embodiment.

FIG. 13 is a view schematically illustrating one example of the state detection device 50 provided in the engine 30 according to the present embodiment. FIG. 13 is a schematic view in which the engine 30 according to the present embodiment is seen from a side.

The engine 30 includes a storing chamber 31 in which a lubricating oil is stored. The storing chamber 31 includes an internal space of an oil pan 32 provided in a lower part of the engine 30. The storing chamber of the oil pan 32 stores a lubricating oil dropped from a component of the engine 30.

A suction member 33 having a suction port 33M to suck the lubricating oil in the oil pan 32 is provided. The suction member 33 includes a tube having an inner flow channel through which the lubricating oil can run. The suction port 33M has an opening provided in one end part of the tube. In the present embodiment, an oil strainer 34 is arranged in the suction port 33M. The suction member 33 sucks the lubricating oil in the storing chamber of the oil pan 32 through the oil strainer 34.

An oil pump 35 is provided in the suction member 33. By operation of the oil pump 35, the lubricating oil in the oil pan 32 is sucked from the suction port 33M. The lubricating oil sucked by the suction member 33 is supplied to the component of the engine 30.

The component of the engine 30, for example, includes a rotary member such as a bearing, and a sliding member such as a gear or a piston. The lubricating oil supplied to the component of the engine 30 lubricates or cools the component. The lubricating oil supplied to the component of the engine 30 drops from the component and is stored into the storing chamber of the oil pan 32.

In such a manner, the lubricating oil circulates in a circulation path including the storing chamber of the oil pan 32 and the component of the engine 30 by operation of the oil pump 35 in the present embodiment.

The storing chamber of the oil pan 32 has a bottom part 32B. A state detection device 50 described in the above-described embodiment is provided in the bottom part 32B. With this arrangement, the state detection device 50 can detect a state of the lubricating oil in the engine 30.

Note that it is assumed in each of the above-described embodiments that image data acquired by a photographing device 60 is transmitted to a server 110. After image data acquired by the photographing device 60 is acquired by an image data acquisition unit 21A of a control device 20 of an excavator 1, a determination unit 21C of the control device 20 may determine a state of a hydraulic oil on the basis of the image data acquired by the photographing device 60. Also, the image data acquired by the image data acquisition unit 21A and determination data indicating a result of the determination by the determination unit 21C may be displayed on a display device 15 provided in the excavator 1. With this arrangement, a driver of the excavator 1 can grasp a state of a hydraulic oil in a hydraulic system 40 of the excavator 1 by looking at display data displayed on the display device 15 after key-on, for example. The driver can take measures such as performance of work of changing a hydraulic oil.

Note that in each of the above-described embodiments, a communication terminal 300 may have a function of a determination unit 21D.

Note that it is assumed in each of the above-described embodiments that a work machine 1 is an excavator. The work machine 1 may be a work machine different from the excavator. The work machine 1 may be, for example, at least one of a bulldozer, a wheel loader, a dump truck, and a forklift.

Note that in the above-described embodiments, determination of a state of oil including at least one of a hydraulic oil and a lubricating oil may be performed by an administrator who looks at image data displayed on a display device 120 or a driver who looks at image data displayed on a display device 15.

REFERENCE SIGNS LIST

1 EXCAVATOR (WORK MACHINE)
2 WORKING EQUIPMENT
3 HYDRAULIC CYLINDER
4 SWINGING BODY
5 TRAVELING BODY
6 BOOM
7 ARM
8 BUCKET
10 BOOM CYLINDER
11 ARM CYLINDER
12 BUCKET CYLINDER
15 DISPLAY DEVICE
20 CONTROL DEVICE
21 ARITHMETIC PROCESSING DEVICE
21A IMAGE DATA ACQUISITION UNIT
21B IMAGE PROCESSING UNIT
21C DETERMINATION UNIT
21D OUTPUT UNIT
21E LIGHTING CONTROL UNIT
21F DISPLAY CONTROL UNIT
22 STORAGE DEVICE
23 INPUT/OUTPUT INTERFACE
30 ENGINE
40 HYDRAULIC SYSTEM
41 HYDRAULIC PUMP
42 PIPELINE
43 HYDRAULIC MOTOR
44 HYDRAULIC OIL TANK
45 PIPELINE
46 PIPELINE
47 OPENING
48 MAIN VALVE
50 STATE DETECTION DEVICE
51 PLUG
51A SHAFT PART
51B FLANGE PART
51C HEAD PART
51D CAP ATTACHMENT PART
51E SCREW THREAD
51F SCREW THREAD
52 SPACER MEMBER
52A LEADING END SURFACE
52B BASE END SURFACE
52C OUTER PERIPHERAL SURFACE
53 ATTACHMENT HOLE
53A GROMMET FITTING HOLE PART
53B FIRST HOUSING HOLE PART
53C SECOND HOUSING HOLE PART
53D PRESSURE-RECEIVING SURFACE
54 SEALING MEMBER
55 GROMMET
56 CAP MEMBER
57 HOLDING MEMBER
57A CYLINDRICAL PART
57B FLOW CHANNEL PART
57C HOLDING PART
57D SEAL GROOVE
57E SEAL GROOVE
58 OPENING
59 SEALING MEMBER
60 PHOTOGRAPHING DEVICE
61 OPTICAL SYSTEM
62 IMAGE SENSOR
70 LIGHTING DEVICE
80 INDEX MEMBER
80S SURFACE
80T REAR SURFACE
90 LIGHTING DEVICE
100 MANAGEMENT SYSTEM
110 SERVER
111 ARITHMETIC PROCESSING DEVICE
111A IMAGE DATA ACQUISITION UNIT
111B IMAGE PROCESSING UNIT
111C DETERMINATION UNIT
111D OUTPUT UNIT
111F DISPLAY CONTROL UNIT
112 STORAGE DEVICE
113 INPUT/OUTPUT INTERFACE
120 DISPLAY DEVICE
200 COMMUNICATION SYSTEM
201 WIRELESS COMMUNICATION DEVICE
202 WIRELESS COMMUNICATION DEVICE
203 WIRELESS COMMUNICATION DEVICE
300 COMMUNICATION TERMINAL
301 CONTROL DEVICE
302 DISPLAY DEVICE
FL OPTICAL PATH
M MARK
M0 REFERENCE MARK
M1 FIRST MARK
M2 SECOND MARK
M3 THIRD MARK
M4 FOURTH MARK
M5 FIFTH MARK
M6 SIXTH MARK
M7 SEVENTH MARK
M8 EIGHTH MARK

The invention claimed is:

1. An oil state detection device comprising:
an index member;
a lighting device that illuminates the index member; and
a photographing device that photographs the index member through oil in a machine device,
wherein the index member has a mark for determination of transparency of the oil, and
a state of the oil is determined on the basis of image data of the mark which data is acquired by the photographing device.

2. The oil state detection device according to claim 1, wherein the index member has a plurality of the marks, and
at least one of density, luminosity, and chroma of the plurality of marks is different from each other.

3. The oil state detection device according to claim 1, wherein the photographing device photographs a surface of the index member, said surface arranged in each of a plurality of positions at different distances to the photographing device, and
a state of the oil is determined on the basis of image data of the index member arranged in each of the plurality of positions.

4. The oil state detection device according to claim 1, further comprising
a plug that supports the photographing device, and
a spacer member supported by the plug,
wherein the index member is immersed in the oil stored in an internal space of the machine device, and the photographing device photographs the index member through the oil and the spacer member.

5. The oil state detection device according to claim 4, further comprising
a holding member that is coupled to the plug and holds the index member in such a manner as to face the spacer member.

6. The oil state detection device according to claim 4,
wherein the plug is arranged in an opening that connects the internal space and an external space of the machine device, and
the photographing device is arranged in the external space.

7. A work machine comprising:
the oil state detection device according to claim 1; and
a determination unit that determines a state of the oil on the basis of image data acquired by the photographing device of the oil state detection device.

8. A management system comprising:
the oil state detection device according to claim 1; and
a determination unit that determines a state of the oil on the basis of image data acquired by the photographing device of the oil state detection device.

9. An oil state detection device comprising:
an index member;
a lighting device that illuminates the index member; and
a photographing device that photographs the index member through oil in a machine device,
wherein the lighting device emits a plurality of pieces of different colored light directed to the index member,
the photographing device receives the colored light reflected from the index member, and
a state of the oil is determined on the basis of the reflection light.

10. An oil state detection method comprising:
illuminating an index member having a mark for determination of transparency of oil through oil in a machine device; and
photographing the index member through the oil,
wherein a state of the oil is determined on the basis of image data of the mark.

* * * * *